US010517999B2

(12) United States Patent
Kummailil et al.

(10) Patent No.: US 10,517,999 B2
(45) Date of Patent: Dec. 31, 2019

(54) HYDROPHILIC COATINGS THROUGH IN SITU SURFACE POLYMERIZATION

(71) Applicant: Cardiac Pacemakers, Inc., St. Paul, MN (US)

(72) Inventors: John Kummailil, Sherborn, MA (US); Paul V. Grosso, Maple Grove, MN (US); Joseph T. Delaney, Jr., Minneapolis, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 168 days.

(21) Appl. No.: 15/485,390

(22) Filed: Apr. 12, 2017

(65) Prior Publication Data

US 2017/0290955 A1 Oct. 12, 2017

Related U.S. Application Data

(60) Provisional application No. 62/321,633, filed on Apr. 12, 2016.

(51) Int. Cl.
| | |
|---|---|
| *A61L 29/06* | (2006.01) |
| *A61L 29/08* | (2006.01) |
| *A61L 29/14* | (2006.01) |
| *A61L 31/10* | (2006.01) |
| *A61L 31/14* | (2006.01) |
| *B05D 1/00* | (2006.01) |
| *B05D 1/02* | (2006.01) |
| *B05D 1/18* | (2006.01) |
| *C08J 7/04* | (2006.01) |
| *C09D 139/06* | (2006.01) |

(52) U.S. Cl.
CPC .......... *A61L 29/085* (2013.01); *A61L 29/06* (2013.01); *A61L 29/14* (2013.01); *A61L 31/10* (2013.01); *A61L 31/14* (2013.01); *B05D 1/005* (2013.01); *B05D 1/02* (2013.01); *B05D 1/18* (2013.01); *C08J 7/042* (2013.01); *C08J 7/047* (2013.01); *C09D 139/06* (2013.01); *A61L 2400/10* (2013.01); *A61L 2420/02* (2013.01); *A61L 2420/08* (2013.01); *C08J 2377/02* (2013.01); *C08J 2439/06* (2013.01)

(58) Field of Classification Search
None
See application file for complete search history.

(56) References Cited

U.S. PATENT DOCUMENTS

| | | | | | |
|---|---|---|---|---|---|
| 3,544,500 | A | * | 12/1970 | Moody | B01J 2/006 427/213.3 |
| 8,158,192 | B2 | * | 4/2012 | Bothe | A61L 27/34 206/5.1 |
| 8,389,083 | B2 | | 3/2013 | Atanasoska et al. | |
| 8,728,508 | B2 | * | 5/2014 | Nielsen | C08J 7/047 424/422 |
| 2003/0236514 | A1 | | 12/2003 | Schwarz | |
| 2004/0121037 | A1 | | 6/2004 | Rouns et al. | |
| 2006/0111546 | A1 | * | 5/2006 | Pacetti | A61L 31/10 528/190 |
| 2006/0147412 | A1 | * | 7/2006 | Hossainy | C08B 37/0072 424/78.27 |
| 2006/0160985 | A1 | * | 7/2006 | Pacetti | A61L 31/10 528/272 |
| 2006/0240065 | A1 | * | 10/2006 | Chen | A61L 31/10 424/423 |
| 2006/0246109 | A1 | * | 11/2006 | Hossainy | A61L 31/10 424/426 |
| 2006/0251694 | A1 | * | 11/2006 | Nielsen | A61L 29/085 424/422 |
| 2007/0184275 | A1 | * | 8/2007 | Gilman | A61L 27/34 428/411.1 |
| 2008/0152800 | A1 | * | 6/2008 | Bothe | A61L 27/34 351/159.33 |
| 2009/0060970 | A1 | * | 3/2009 | Toner | A61K 9/0024 424/423 |
| 2009/0285974 | A1 | * | 11/2009 | Kerrigan | A61L 31/14 427/2.21 |
| 2010/0100009 | A1 | * | 4/2010 | Nielsen | A61L 29/085 600/585 |
| 2011/0086081 | A1 | * | 4/2011 | To | A61F 2/82 424/423 |
| 2012/0321778 | A1 | * | 12/2012 | Kerrigan | A61L 31/14 427/2.25 |
| 2012/0328769 | A1 | * | 12/2012 | Kerrigan | A61L 31/14 427/2.3 |
| 2013/0323291 | A1 | | 12/2013 | Li et al. | |

FOREIGN PATENT DOCUMENTS

| | | |
|---|---|---|
| CN | 102925425 A | 2/2013 |
| FR | 1504833 A | 12/1967 |
| WO | WO199858990 A1 | 12/1998 |

OTHER PUBLICATIONS

Surface Functionalization of polypropylene film via UV-induce photografting of N-vinylpyrollidone / Maleic anhydride binary monomers, Xing et al., Macromol. Chem. Phys. 2005, 206, 1106-1113. Hereinafter Xing (Year: 2005).*

(Continued)

*Primary Examiner* — Peter A Salamon

(74) *Attorney, Agent, or Firm* — Faegre Baker Daniels LLP

(57) ABSTRACT

A medical device for insertion or implantation in a body includes a polymer substrate and a layer of poly(vinyl pyrrolidone-alt-maleic anhydride) formed on a surface of the polymer substrate. Polymer chains of the poly(vinyl pyrrolidone-alt-maleic anhydride) are entangled with the polymer substrate.

12 Claims, No Drawings

(56) References Cited

OTHER PUBLICATIONS

International Search Report and Written Opinion issued in PCT/US2017/027106, dated Jul. 14, 2017, 13 pages.
Desai, Shrojal M., et al. "Fabrication of Long-Term Hydrophilic Elastomeric Surfaces Via Plasma Induced Surface Cross-Linking of Functional Monomers." Surface and Coatings Technology, 184:6-12, 2004.
Xing, Chang-Min, et al. "Surface Functionalization of Polypropylene Film via UV-Induced Photografting of N-Vinylpyrrolidone/Maleic Anhydride Binary Monomers." Macromolecular Chemistry and Physics, 206(11):1106-1113, 2005.

* cited by examiner

HYDROPHILIC COATINGS THROUGH IN SITU SURFACE POLYMERIZATION

CROSS-REFERENCE TO RELATED APPLICATION

This application claims priority to Provisional Application No. 62/321,633, filed Apr. 12, 2016, which is herein incorporated by reference in its entirety.

TECHNICAL FIELD

The present invention relates to coatings for implantable or insertable medical devices. More specifically, the invention relates to lubricious, hydrophilic coatings and methods of forming lubricious, hydrophilic coatings on polymer substrates of medical devices.

BACKGROUND

Implantable or insertable medical devices often employ lubricious, hydrophilic polymer coatings to permit the devices to be easily inserted and maneuvered within a patient's body. Examples of such medical devices can include electrical leads, guide catheters, and angioplasty balloon dilation catheters. The lubricious, hydrophilic polymer coatings absorb water, either prior to insertion or from a patient's bodily fluids, and become slippery, reducing the friction between the devices and surrounding tissues.

SUMMARY

Example 1 is a medical device for insertion or implantation in a body. The medical device includes a polymer substrate and a layer of poly(vinyl pyrrolidone-alt-maleic anhydride) formed on a surface of the polymer substrate. Polymer chains of the poly(vinyl pyrrolidone-alt-maleic anhydride) are entangled with the polymer substrate.

In Example 2, the medical device of Example 1, further including a polymer top coat disposed on the layer of poly(vinyl pyrrolidone-alt-maleic anhydride).

In Example 3, the medical device of either of examples 1 or 2, wherein the polymer substrate is Nylon 12 or a polymer based on Nylon 12.

In Example 4, the medical device of any of Examples 1-3, wherein the layer of poly(vinyl pyrrolidone-alt-maleic anhydride) is covalently bonded to the polymer substrate.

In Example 5, the medical device of any of Examples 1-4, wherein the layer of poly(vinyl pyrrolidone-alt-maleic anhydride) is free of a radical initiator compound residue.

In Example 6, the medical device of any of Examples 1-4, wherein the layer of poly(vinyl pyrrolidone-alt-maleic anhydride) includes a radical initiator compound residue including at least one of a photo initiator compound residue and a thermal initiator compound residue.

In Example 7, the medical device of any of Examples 1-4, wherein the layer of poly(vinyl pyrrolidone-alt-maleic anhydride) includes a residue of a cross-linking compound, wherein the residue from the cross-linking compound cross-links the polymer chains of the poly(vinyl pyrrolidone-alt-maleic anhydride).

Example 8 is method of forming a lubricious, hydrophilic polymer coating on a surface of a polymer substrate of a medical device. The method includes depositing a monomer solution onto the surface of the polymer substrate, the monomer solution including maleic anhydride, a hydrophilic olefinic monomer, and an optional swelling agent, wherein at least one of the hydrophilic olefinic monomer and the optional swelling agent swells the polymer substrate; and polymerizing the maleic anhydride and the hydrophilic olefinic monomer of the monomer solution by radical polymerization to form chains of an alternating copolymer of the maleic anhydride and the hydrophilic olefinic monomer, wherein some of the chains of the alternating copolymer of the maleic anhydride and the hydrophilic olefinic monomer are entangled in the swollen polymer substrate.

In Example 9, the method of Example 8, further comprising treating the polymer surface with a plasma to form free radicals on the surface of the polymer substrate before depositing the monomer solution, wherein the free radicals covalently bond some of the hydrophilic olefinic monomer to the polymer substrate and initiate the radical polymerization of the maleic anhydride and the hydrophilic olefinic monomer to form the alternating copolymer of the maleic anhydride and the hydrophilic olefinic monomer.

In Example 10, the method of either of Examples 8 or 9, wherein the monomer solution further includes a radical initiator compound that generates free radicals when exposed to actinic radiation, and polymerizing the maleic anhydride and the hydrophilic olefinic monomer of the monomer solution includes exposing the radical initiator in the monomer solution to actinic radiation to generate the free radicals to initiate the radical polymerization of the maleic anhydride and the hydrophilic olefinic monomer to form the alternating copolymer of the maleic anhydride and the hydrophilic olefinic monomer.

In Example 11, the method of either of Examples 8 or 9, wherein the monomer solution further includes a radical initiator compound that generates free radicals when exposed to an elevated temperature, and polymerizing the maleic anhydride and the hydrophilic olefinic monomer of the monomer solution includes exposing the radical initiator in the monomer solution to an elevated temperature to generate the free radicals to initiate the radical polymerization of the maleic anhydride and the hydrophilic olefinic monomer to form the alternating copolymer of the maleic anhydride and the hydrophilic olefinic monomer.

In Example 12, the method of any of Examples 8-11, wherein the polymer substrate includes Nylon 12 or a polymer based on Nylon-12.

In Example 13, the method of any of Examples 8-12, wherein the hydrophilic olefinic monomer is N-vinyl pyrrolidone and the alternating copolymer of the maleic anhydride and the hydrophilic olefinic monomer is poly(vinyl pyrrolidone-alt-maleic anhydride).

In Example 14, the method of any of Examples 8-12, wherein the hydrophilic olefinic monomer includes at least one of 2-hydroxyethyl methacrylate and 2-hydroxyethyl ethacrylate, and the monomer solution includes the optional swelling agent.

In Example 15, the method of any of Examples 8-13, wherein the hydrophilic olefinic monomer is able to cause swelling of the polymer substrate and the monomer solution does not include the optional swelling agent.

Example 16 is a medical device for insertion or implantation in a body. The medical device includes a polymer substrate and a layer of poly(vinyl pyrrolidone-alt-maleic anhydride) formed on a surface of the polymer substrate. Polymer chains of the poly(vinyl pyrrolidone-alt-maleic anhydride) are entangled with the polymer substrate to form a lubricious, hydrophilic layer.

In Example 17, the medical device of Example 16, further including a polymer top coat disposed on the layer of poly(vinyl pyrrolidone-alt-maleic anhydride).

In Example 18, the medical device of either of Examples 16 or 17, wherein the polymer substrate is Nylon 12 or a polymer based on Nylon 12.

In Example 19, the medical device of any of Examples 16-18, wherein the layer of poly(vinyl pyrrolidone-alt-maleic anhydride) is covalently bonded to the polymer substrate.

In Example 20, the medical device of any of Examples 16-19, wherein the layer of poly(vinyl pyrrolidone-alt-maleic anhydride) is free of a radical initiator compound residue.

In Example 21, the medical device of any of Examples 16-19, wherein the layer of poly(vinyl pyrrolidone-alt-maleic anhydride) includes a radical initiator compound residue including at least one of a photo initiator compound residue and a thermal initiator compound residue.

In Example 22, the medical device of any of Examples 16-19, wherein the layer of poly(vinyl pyrrolidone-alt-maleic anhydride) includes a residue of a cross-linking compound, wherein the residue of the cross-linking compound cross-links the polymer chains of the poly(vinyl pyrrolidone-alt-maleic anhydride).

Example 23 is a method of forming a lubricious, hydrophilic polymer coating on a surface of a polymer substrate of a medical device. The method includes depositing a monomer solution onto the surface of the polymer substrate, the monomer solution including maleic anhydride, a hydrophilic olefinic monomer, and an optional swelling agent, wherein at least one of the hydrophilic olefinic monomer and the optional swelling agent swells the polymer substrate; and polymerizing the maleic anhydride and the hydrophilic olefinic monomer of the monomer solution by radical polymerization to form chains of an alternating copolymer of the maleic anhydride and the hydrophilic olefinic monomer, wherein some of the chains of the alternating copolymer of the maleic anhydride and the hydrophilic olefinic monomer are entangled in the swollen polymer substrate.

In Example 24, the method of Example 23, further comprising treating the polymer substrate with a plasma to form free radicals on the surface of the polymer substrate before depositing the monomer solution, wherein the free radicals covalently bond some of the hydrophilic olefinic monomer to the polymer substrate and initiate the radical polymerization of the maleic anhydride and the hydrophilic olefinic monomer to form the alternating copolymer of the maleic anhydride and the hydrophilic olefinic monomer.

In Example 25, the method of either of Examples 23 or 24, wherein the monomer solution further includes a radical initiator compound that generates free radicals when exposed to actinic radiation, and polymerizing the maleic anhydride and the hydrophilic olefinic monomer of the monomer solution includes exposing the radical initiator compound in the monomer solution to actinic radiation to generate the free radicals to initiate the radical polymerization of the maleic anhydride and the hydrophilic olefinic monomer to form the alternating copolymer of the maleic anhydride and the hydrophilic olefinic monomer.

In Example 26, the method of either of Examples 23 or 24, wherein the monomer solution further includes a radical initiator compound that generates free radicals when exposed to an elevated temperature, and polymerizing the maleic anhydride and the hydrophilic olefinic monomer of the monomer solution includes exposing the radical initiator compound in the monomer solution to an elevated temperature to generate the free radicals to initiate the radical polymerization of the maleic anhydride and the hydrophilic olefinic monomer to form the alternating copolymer of the maleic anhydride and the hydrophilic olefinic monomer.

In Example 27, the method of any of Examples 23-26, wherein depositing the polymer solution includes at least one of dip coating, spray coating, and spin coating the monomer solution onto the polymer substrate.

In Example 28, the method of any of Examples 23-27, wherein the polymer substrate includes Nylon 12 or a polymer based on Nylon 12.

In Example 29, the method of any of Examples 23-27, wherein the hydrophilic olefinic monomer is N-vinyl pyrrolidone and the alternating copolymer of the maleic anhydride and the hydrophilic olefinic monomer is poly(vinyl pyrrolidone-alt-maleic anhydride).

In Example 30, the method of any of Examples 23-27, wherein the hydrophilic olefinic monomer includes at least one of 2-hydroxyethyl methacrylate and 2-hydroxyethyl ethacrylate, and the monomer solution includes the optional swelling agent.

In Example 31, the method of any of Examples 23-27, wherein the hydrophilic olefinic monomer is able to cause swelling of the polymer substrate and the monomer solution does not include the optional swelling agent.

In Example 32, the method of any of Examples 23-27, wherein polymer substrate includes polyethylene terephthalate, and the optional swelling agent includes benzyl alcohol.

Example 33 is a method of forming a lubricious, hydrophilic polymer coating on a surface of a polymer substrate of an implantable or insertable medical device. The method includes treating the surface of the polymer substrate with a plasma to form free radicals on the surface of the polymer substrate; depositing the monomer solution onto the surface of the polymer substrate to covalently bond a portion of the N-vinyl pyrrolidone monomer to the polymer substrate, the monomer solution including maleic anhydride monomer and N-vinyl pyrrolidone monomer, wherein the N-vinyl pyrrolidone swells the polymer substrate; and polymerizing the maleic anhydride monomer and the N-vinyl pyrrolidone monomer of the monomer solution, wherein the free radicals on the polymer substrate initiate a radical polymerization of the maleic anhydride monomer and the N-vinyl pyrrolidone monomer to form chains of poly(vinyl pyrrolidone-alt-maleic anhydride), wherein some of the chains of the poly(vinyl pyrrolidone-alt-maleic anhydride) are entangled in the swollen polymer substrate to form the lubricious, hydrophilic polymer coating.

In Example 34, the method of Example 33, wherein the polymer substrate includes Nylon 12 or a polymer based on Nylon 12.

In Example 35, the method of either of Examples 33 or 34, further including depositing a polymer top coat on the poly(vinyl pyrrolidone-alt-maleic anhydride) polymer coating.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Commercially available lubricious, hydrophilic polymer coatings for implantable medical devices may not be optimized for use with substrates of the medical devices formed of certain polymers, such as polyethylene terephthalate (PET), Nylon-12, and polymers based on Nylon 12, such as Pebax®. Some polymer coatings can cause one or more components of the polymer substrate to migrate to the surface of the polymer substrate where they may aggregate to form particles which can break away from the surface. Particles formed by this "blooming" of the polymer may expose the patient to undesirable side effects. Some other commercially available polymer coatings may suffer from embrittlement and/or "mudcracking".

Lubricious polymer coatings need to adhere to the underlying polymer substrate of the device to be effective. In addition, should the lubricious polymer coating itself flake off of the device, the dislodged polymer coating material may expose the patient to undesirable side effects. Thus, a lubricious, hydrophilic polymer coating must have good adhesion to the underlying substrate of the medical device, even under abrasive conditions within a body. Achieving such adhesion may be especially challenging when the underlying substrate is a polymer to which lubricious, hydrophilic polymer coatings may not always adhere well, such as Nylon 12.

Embodiments of this disclosure employ radical alternating copolymerization of maleic anhydride monomer and a hydrophilic olefinic monomer to form a durable, lubricious hydrophilic polymer coating on a surface of a polymer substrate. The coating is polymerized in situ from a solution including the monomers and an optional swelling agent, wherein at least one of the hydrophilic olefinic monomer and the optional swelling agent are able to penetrate the surface of the polymer substrate and cause the substrate molecules to move apart, thus swelling the surface of the polymer substrate. Some of the hydrophilic olefinic monomer, which forms part of the hydrophilic polymer coating, is thus entangled with the polymer substrate either by its own ability to swell the surface of the polymer substrate, or by being carried along with the optional swelling agent. Thus, the swelling of the surface of the polymer substrate provides for physical entanglement between the chains of the polymerized coating and the surface of the polymer substrate. The entanglement is enhanced because it can occur early in the polymerization process, while the chains are still short (i.e., oligomers), since the chains are formed in situ from monomers. Shorter polymer chains are believed to be more thermodynamically favorable than longer polymer chains for interaction with the surface of the polymer substrate. The enhanced entanglement provides for improved adhesion of the lubricious, hydrophilic polymer coating to the polymer substrate because scission of the entangled polymer chains is required to separate the polymer coating from the polymer substrate. In contrast, prior art coatings deposited on the surface of the polymer substrate as solutions of homopolymers or copolymers have relatively long polymer chains too large for significant entanglement, and thus may be easily separated from the polymer surface.

The at least one of the hydrophilic olefinic monomer and the optional swelling agent are able to penetrate the surface by virtue of having solubility parameters that are close to those of the polymer substrate. Swelling may be determined by, for example, gravimetric measurement. Gravimetric measurement may be performed by comparing the weight of a sample of the polymer substrate material before and after exposure to the hydrophilic olefinic monomer or the optional swelling agent.

In some embodiments, forming a lubricious, hydrophilic polymer coating on a surface of a polymer substrate of a medical device begins with preparing a monomer solution including maleic anhydride monomers and hydrophilic olefinic monomers. In some embodiments, depending on the nature of the polymer substrate and the hydrophilic olefinic monomer, the hydrophilic olefinic monomer itself may be able to swell the surface of the polymer substrate and the optional swelling agent may not be necessary for swelling the surface of the polymer substrate. In other embodiments, the hydrophilic olefinic monomer cannot swell the surface of the polymer substrate, and the monomer solution further includes the optional swelling agent able to create swelling of the surface of the polymer substrate. In still other embodiments, in which the hydrophilic olefinic monomer can swell the surface of the polymer substrate, the optional swelling agent may be employed to enhance swelling of the polymer substrate, further enhancing entanglement of the chains of the polymerized coating with the surface of the polymer substrate.

For example, in embodiments in which the polymer substrate can be Nylon-12 (or a copolymer including blocks of Nylon-12, such as Pebax®), the hydrophilic olefinic monomer can be N-vinyl pyrrolidone and the optional swelling agent may be unnecessary because the N-vinyl pyrrolidone can swell the Nylon-12 substrate. In other embodiments in which the polymer substrate can be PET, the hydrophilic olefinic monomer can be N-vinyl pyrrolidone which may not swell the PET substrate and an optional swelling agent able to swell the PET substrate, such as benzyl alcohol, can be added to the monomer solution.

In another exemplary embodiment, in which the polymer substrate can be Nylon-12 (or a copolymer including blocks of Nylon-12, such as Pebax®), the hydrophilic olefinic monomer can include at least one of 2-hydroxyethyl methacrylate and 2-hydroxyethyl ethacrylate, and the monomer solution includes the optional swelling agent able to create swelling of the surface of the polymer substrate. Examples of suitable optional swelling agents for swelling Nylon-12 (or a copolymer including blocks of Nylon-12, such as Pebax®) can include dimethylformamide (DMF), N,N-dimethylacetamide (DMAC), and tetrahydrofuran (THF).

In some embodiments, the monomer solution may further include a radical initiator compound that generates free radicals when exposed to energy, such as actinic radiation or an elevated temperature. The free radicals can initiate the polymerization of the coating, as described below. Examples of suitable UV initiator compounds include (4-bromophenyl)diphenylsulfonium triflate, (4-fluorophenyl)diphenylsulfonium triflate, (4-iodophenyl)diphenylsulfonium triflate, (4-methoxyphenyl)diphenylsulfonium triflate, (4-methylphenyl)diphenylsulfonium triflate, (4-methylthiophenyl)methyl phenyl sulfonium triflate, (4-phenoxyphenyl)diphenylsulfonium triflate, (4-phenylthiophenyl)diphenylsulfonium triflate, (4-tert-butylphenyl)diphenylsulfonium triflate, (cumene)cyclopentadienyliron (II) hexafluorophosphate, (tert-butoxycarbonylmethoxynaphthyl)-diphenylsulfonium triflate, 1-naphthyl diphenylsulfonium triflate, 2-(4-methoxystyryl)-4,6-bis(trichloromethyl)-1,3,5-triazine, bis(4-tert-butylphenyl)iodonium perfluoro-1-butanesulfonate, bis(4-tert-butylphenyl)iodonium p-toluenesulfonate, bis(4-tert-butylphenyl)iodonium triflate, boc-methoxyphenyldiphenylsulfonium triflate, diphenyliodonium hexafluorophosphate, diphenyliodonium nitrate, diphenyliodonium perfluoro-1-butanesulfonate, diphenyliodonium p-toluenesulfonate, diphenyliodonium triflate, N-hydroxy-5-norbornene-2,3-dicarboximide perfluoro-1-butanesulfonate, N-hydroxynaphthalimide triflate, triarylsulfonium hexafluoroantimonate salts, triphenylsulfonium perfluoro-1-butanesufonate, triphenylsulfonium triflate, tris(4-tert-butylphenyl)sulfonium perfluoro-1-butanesulfonate, and tris(4-tert-butylphenyl)sulfonium triflate. Examples of suitable thermal initiator compounds include azobisisobutyronitrile (AIBN), dibenzoyl peroxide, N-benzyl pyridinium bromide, N-benzyl o-cyano pyridinium bromide, N-benzyl p-cyanopyridinium bromide, N-benzyl N, N-dimethyl anilinium bromide, and benzyl triphenyl phosphonium bromide.

In some embodiments, the monomer solution may further include a cross-linking compound. The cross-linking compound can cross-link chains of the polymerized coating to enhance the mechanical strength of the lubricious, hydrophilic polymerized coating. Cross-linking also greatly increases the molecular weight of the polymer coating such that chain scission requiring large amounts of energy is necessary for delamination. Suitable cross-linking compounds are miscible with the other monomers, have olefinic bonds that may polymerize under conditions suitable for the other components, and have a functionality of polymerizable olefinic bonds per molecule greater than one. Examples of suitable cross-linking compounds include PEG diacrylate, PEG dimethacrylate, and neopentylglycol diacrylate.

The monomer solution can be deposited onto the surface of the polymer substrate for example by dip coating, spray coating, or spin coating. Once the monomer solution is deposited onto the surface, the hydrophilic olefinic monomer and/or the optional swelling agent swells the surface of the polymer substrate. In embodiments including a UV radical initiator compound in the monomer solution, the deposited monomer solution can be exposed to UV radiation to generate free radicals and initiate polymerization of the monomers. In embodiments including a thermal radical initiator compound in the monomer solution, the deposited monomer solution can be exposed to an elevated temperature to generate free radicals and initiate polymerization of the monomers. In either case, generation of the free radicals can be delayed as necessary by delaying exposure to UV radiation or to an elevated temperature, to provide adequate time for at least one of the hydrophilic olefinic monomer and the optional swelling agent to swell the surface of the polymer substrate.

As the free radicals initiate polymerization of the maleic anhydride monomer and a hydrophilic olefinic monomer, polymer chains of an alternating copolymer of the maleic anhydride and the hydrophilic olefinic monomer are formed. Alternating copolymers are copolymers having a structure of alternating monomers. The polymer chains are short to begin with, as they are formed from the monomers. The short polymer chains are able to entangle extensively with the swollen surface of the polymer substrate, due to their small size. As the polymerization continues and the short polymer chains grow to long polymer chains, they remain mechanically locked to the surface of the polymer substrate, providing enhanced adhesion between the polymer coating and the polymer substrate. In some embodiments, a residue of the radical initiator compound can remain in the layer of alternating copolymer of the maleic anhydride and the hydrophilic olefinic monomer.

In some embodiments, adhesion between the polymer coating and the polymer substrate is further enhanced by the formation of covalent bonds between the polymer coating and the polymer substrate. In such embodiments, forming the lubricious, hydrophilic polymer coating on the surface of the polymer substrate of the medical device further includes treating the surface of the polymer substrate with a plasma before depositing the monomer solution. Without wishing to be bound by any theory, it is believed that the plasma forms sites having free radicals on the surface of the polymer substrate. Some of the hydrophilic olefinic monomer molecules in the monomer solution can covalently bond to the surface of the polymer substrate at the free radical sites. Each of the bonded hydrophilic olefinic monomer molecules can have a free radical site available for bonding to a molecule of the maleic anhydride as the free radical propagates. Each of the bonded maleic anhydride molecules can have a free radical site available for bonding to another molecule of the hydrophilic olefinic monomer as the free radical continues to propagate along the polymer. The propagation of the free radical in this manner forms the alternating copolymer of the maleic anhydride and the hydrophilic olefinic monomer, while the copolymer remains covalently bonded to the surface of the polymer substrate. In such embodiments, the resulting layer of polymer coating may be free of any radical initiator compound residue because no radical initiator compound may be necessary for formation of the alternating copolymer of the maleic anhydride.

The free radical sites formed on the surface of the polymer substrate by the plasma treatment can begin to degrade after treatment, as the free radicals react with other molecules in the environment before deposition of the monomer solution. Thus, the time delay between the plasma treatment and the deposition of the monomer solution should be as short as possible, for example less than 60 minutes, less than 50 minutes, less than 40 minutes, less than 30 minutes, less than 20 minutes, less than 10 minutes, or less than any time between any of the forgoing times.

In some embodiments including treating the polymer substrate with the plasma before depositing the monomer solution, the monomer solution may further include the radical initiator compound as described above. In such embodiments, short polymer chains can be formed covalently bonded to the surface of the polymer substrate as described above, and then the polymer chains lengthened at an accelerated rate by free radicals generated by the radical initiator compound following the initial covalent bonding and polymerization.

In embodiments including the cross-linking agent, the free radicals generated from the UV radical initiator compound, the thermal radical initiator compound, plasma exposure of the polymer substrate prior to deposition of the monomer solution, or a combination of any of these, can also serve to bond the cross-linking agent to the polymer chains of the alternating copolymer of the maleic anhydride and the hydrophilic olefinic monomer to cross-link the polymer chains. In such embodiments, a residue of the cross-linking compound can remain in the layer of alternating copolymer of the maleic anhydride and the hydrophilic olefinic monomer.

An exemplary embodiment, forming a lubricious, hydrophilic polymer coating on a surface of a polymer substrate of an implantable or insertable medical device begins with preparing a monomer solution including maleic anhydride monomer and N-vinyl pyrrolidone monomer in a stoichiometric ratio of 1:1. Next, the surface of the polymer substrate can be treated a plasma to form free radicals on the surface of the polymer substrate. After the plasma treatment, the monomer solution can be deposited onto the surface of the polymer substrate to swell the surface of the polymer substrate while a portion of the N-vinyl pyrrolidone monomer covalently bonds to the surface of the polymer substrate. As the free radicals on the surface of the polymer substrate initiate radical polymerization of the N-vinyl pyrrolidone and the maleic anhydride, chains of poly(vinyl pyrrolidone-alt-maleic anhydride) are formed, including chains of poly (vinyl pyrrolidone-alt-maleic anhydride) covalently bonded to the polymer substrate. Some of the chains of poly(vinyl pyrrolidone-alt-maleic anhydride) become entangled in the swollen surface of the polymer substrate, as described above, to form the lubricious, hydrophilic coating.

In some embodiments, the enhanced adhesion between the polymer coating and the polymer substrate provided as described above due to enhanced entanglement between polymer chains of the polymer coating, and optionally due to the covalent bonding between the polymer chains and the polymer coating, may enable bonding of another polymer layer, or top coat, to the medical device. In some embodiments, the top coat may not directly bond well to the polymer substrate, but may bond well to the polymer coating. In such embodiments, the polymer coating may act as a tie layer, bonding the top coat to the polymer substrate of the medical device. Examples of suitable top coats for use with, for example, poly(vinyl pyrrolidone-alt-maleic anhydride), may include poly(vinyl acetate), poly(vinylpyrrolidone), or poly(acrylic acid).

Embodiments described above may be employed to provide a lubricious, hydrophilic coating to a surface of a polymer substrate for any implantable or insertable medical device. Exemplary medical devices can include implantable electrical leads, implantable catheters, guide catheters, and angioplasty balloon dilation catheters.

Examples

The present invention is more particularly described in the following examples that are intended as illustrations only, since numerous modifications and variations within the scope of the present invention will be apparent to those of skill in the art. Unless otherwise noted, all parts, percentages, and ratios reported in the following examples are on a weight bases, and all reagents used in the examples were obtained, or are available, from the chemical suppliers described below, or may be synthesized by conventional techniques.

Formation of a Hydrophilic Polymer Coating of Poly(Vinyl Pyrrolidone-Alt-Maleic Anhydride)

10 grams (g) of maleic anhydride pellets (Sigma Aldrich®, CAS #108-31-6) were added to 11.37 g of 1-vinyl-2-pyrrolidinone (NVP) (Sigma Aldrich®, CAS #88-12-0). The combination was heated to 50° C. and gently shaken for several minutes until the maleic anhydride was fully dissolved. The resulting solution was straw-colored, transparent, and of negligible viscosity. To the solution of maleic anhydride and NVP, 10 milligrams (mg) of azobisisobutyronitrile (AIBN) (Sigma Aldrich®, CAS Number 78-67-1) free radical initiator was added. The AIBN dissolved almost instantly. The resulting solution was the applied to sheets of a thermoplastic polyurethane elastomer (Pellethane® TPU 2363-55D). The coated sheets became noticeably less translucent and more transparent, as well as less stiff and more rubbery. These changes demonstrated that some degree of plasticization had occurred, indicating that the monomers and low molecular weight oligomers had penetrated into the polymer matrix of the thermoplastic polyurethane elastomer. The coated sheets were then heated to 60° C. under a nitrogen stream for an hour to polymerize the solution. The resulting polymerized coated surface of the sheets was solid and became highly lubricious when wetted.

The sheets with the polymerized coated surface underwent an exhaustive Soxhlet extraction in water to test the durability of the coating, and then air dried. The polymerized coated surface of the sheets remained highly lubricious and hydrophilic when wetted. Thus, the polymer network of the coating was found to be quite durable and, thus, appears to be entangled with the thermoplastic polyurethane elastomer substrate.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device for insertion or implantation in a body, the medical device comprising:
   a polymer substrate; and
   a layer of poly(vinyl pyrrolidone-alt-maleic anhydride) formed on a surface of the polymer substrate, wherein polymer chains of the poly(vinyl pyrrolidone-alt-maleic anhydride) are entangled with the polymer substrate to form a lubricious, hydrophilic layer, the polymer chains cross-linked with a cross-linking compound including at least one compound selected from the group of poly(ethylene glycol) diacrylate, poly(ethylene glycol) dimethacrylate and neopentylglycol diacrylate.

2. The medical device of claim 1, further including a polymer top coat disposed on the layer of poly(vinyl pyrrolidone-alt-maleic anhydride).

3. The medical device of claim 1, wherein the polymer substrate is Nylon 12 or a polymer based on Nylon 12.

4. The medical device of claim 1, wherein the layer of poly(vinyl pyrrolidone-alt-maleic anhydride) is covalently bonded to the polymer substrate.

5. The medical device of claim 1, wherein the layer of poly(vinyl pyrrolidone-alt-maleic anhydride) is free of a radical initiator compound residue.

6. The medical device of claim 1, wherein the layer of poly(vinyl pyrrolidone-alt-maleic anhydride) includes a radical initiator compound residue including at least one of a photo initiator compound residue and a thermal initiator compound residue.

7. A medical device for insertion or implantation in a body, the medical device comprising:
   a polymer substrate;
   a layer of poly(vinyl pyrrolidone-alt-maleic anhydride) formed on a surface of the polymer substrate, wherein polymer chains of the poly(vinyl pyrrolidone-alt-maleic anhydride) are entangled with the polymer substrate to form a lubricious, hydrophilic layer; and
   a polymer layer disposed on the layer of poly(vinyl pyrrolidone-alt-maleic anhydride), the polymer layer including at least one polymer selected from the group of poly(vinyl acetate), poly(vinylpyrrolidone) and poly(acrylic acid).

8. The medical device of claim 7, wherein the polymer substrate is Nylon 12 or a polymer based on Nylon 12.

9. The medical device of claim 7, wherein the layer of poly(vinyl pyrrolidone-alt-maleic anhydride) is covalently bonded to the polymer substrate.

10. The medical device of claim 7, wherein the layer of poly(vinyl pyrrolidone-alt-maleic anhydride) is free of a radical initiator compound residue.

11. The medical device of claim 7, wherein the layer of poly(vinyl pyrrolidone-alt-maleic anhydride) includes a radical initiator compound residue including at least one of a photo initiator compound residue and a thermal initiator compound residue.

12. The medical device of claim 7, wherein the layer of poly(vinyl pyrrolidone-alt-maleic anhydride) includes a residue of a cross-linking compound, wherein the residue of the cross-linking compound cross-links the polymer chains of the poly(vinyl pyrrolidone-alt-maleic anhydride).

* * * * *